(12) United States Patent
Albrecht

(10) Patent No.: US 6,346,552 B1
(45) Date of Patent: Feb. 12, 2002

(54) BREATHING GAS MIXTURE CONTAINING PERFLUOROCARBONS

(75) Inventor: Detlev Michael Albrecht, Dresden (DE)

(73) Assignee: Dräger Medizintechnik GmbH (DE)

( * ) Notice: Subject to any disclaimer, the term of this patent is extended or adjusted under 35 U.S.C. 154(b) by 0 days.

(21) Appl. No.: 09/320,310

(22) Filed: May 26, 1999

(30) Foreign Application Priority Data

May 27, 1998 (DE) .......................................... 198 23 606

(51) Int. Cl.[7] .............................................. A61K 47/00
(52) U.S. Cl. ...................................................... 514/771
(58) Field of Search ........................................ 514/771

(56) References Cited

U.S. PATENT DOCUMENTS

| | | | |
|---|---|---|---|
| 5,228,434 A | 7/1993 | Fishman | 514/425 |
| 5,470,885 A * | 11/1995 | Fuhrman et al. | 514/743 |
| 5,674,913 A | 10/1997 | Clark, Jr. | 514/731 |
| 5,733,939 A | 3/1998 | Fuhrman et al. | 514/310 |

OTHER PUBLICATIONS

Kruger et al., "Segregation in fluorocarbon–hydrocarbon solutions", J. Solution Chem. 11(10), pp. 719–728, 1982.*

* cited by examiner

*Primary Examiner*—Dwayne C. Jones
(74) *Attorney, Agent, or Firm*—McGlew and Tutle, P.C.

(57) ABSTRACT

A breathing gas mixture is provided for the treatment of lung diseases, containing an amount of perfluorocarbon and oxygen containing 5 vol. % to 40 vol. % of perfluorocarbon relative to the amount of perfluorocarbon and oxygen. The amount of perfluorocarbon and oxygen in the breathing gas mixture ranges from about 20 vol. % to a maximum of 100 vol. % of the breathing gas mixture, and the remaining amount of up to about 80 vol. % contains one or more of the gases nitrogen, nitrogen monoxide and/or one or more anesthesia gases or noble gases, especially xenon. Perfluorohexane is an especially preferred perfluorocarbon.

13 Claims, 1 Drawing Sheet

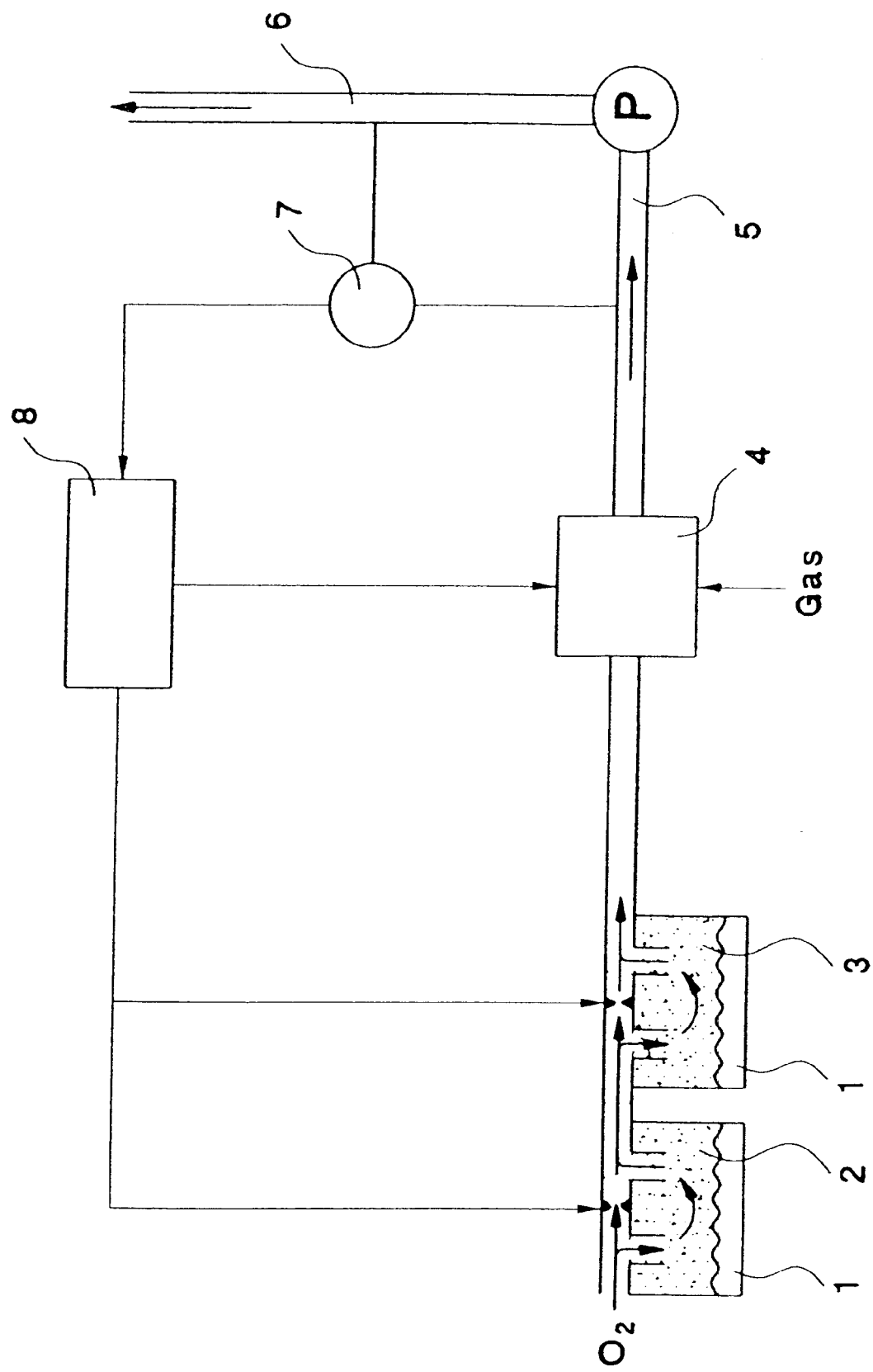

BREATHING GAS MIXTURE CONTAINING PERFLUOROCARBONS

FIELD OF THE INVENTION

The present invention pertains to a breathing gas mixture and to a device for metering a breathing gas mixture.

BACKGROUND OF THE INVENTION

Various breathing gas mixtures, which may be used for various applications in medicine, have been described in the literature. For example, U.S. Pat. No. 5,228,434 discloses a breathing gas mixture containing xenon, oxygen and helium, which is said to be used in anesthesia.

Liquid perfluorocarbons were hitherto introduced into the lungs of a human patient or mammal for the treatment of lung diseases associated with severe gas exchange disturbances, especially ARDS (Adult Respiratory Distress Syndrome) and pneumonia, and the patient or the mammal was respirated by means of a conventional respirator during that time.

It was observed that perfluorocarbons are able, in principle, to substantially improve the gas exchange and especially the $O_2/CO_2$ exchange in the lungs.

However, one fundamental problem of the current clinical use of liquid perfluorocarbons is the fact that it is not possible to accurately meter the liquid perfluorocarbons. In addition, increased respiration pressures are necessary for respirating the partially liquid-filled lungs, as a result of which adverse effects may in turn be induced in the patient.

SUMMARY AND OBJECTS OF THE INVENTION

The object of the present invention is to provide a breathing gas mixture for the treatment of lung diseases and a device for metering same in order to make possible an improved, accurate and reproducible metering for the treatment of lung diseases.

According to the invention, a breathing gas mixture is provided containing an amount of perfluorocarbon and oxygen with 5 vol. % to 40 vol. % relative to the amount of perfluorocarbon and oxygen. The percentage of perfluorocarbon and oxygen in the breathing gas mixture is preferably about 20 vol. % to 100 vol. % of the breathing gas mixture and the remaining part of up to about 80 vol. % preferably contains one or more of the gases nitrogen, nitrogen monoxide and/or one or more anesthesia gases or noble gases, especially xenon. The perfluorocarbon preferably comprises one or more of the compounds perfluoropentane, perfluorohexane, and perfluorooctane, wherein perfluoropentane or perfluorohexane is especially preferred.

According to another aspect of the invention, a device is provided for metering a breathing gas mixture as mentioned above. The device has one or more evaporators connected in series for evaporating the liquid perfluorocarbon. There is a gas flow connection to an inspiration line of an anesthesia apparatus or respirator, which gas connection is arranged downstream of the evaporator or evaporators.

A measuring cell is preferably provided for determining the concentration of the perfluorocarbon in the breathing gas mixture. The concentration signal is used to set the perfluorocarbon concentration in the breathing gas mixture via one or more final control elements at the evaporator or evaporators, especially after comparison with corresponding set points. The measuring cell for determining the concentration of the perfluorocarbon in the breathing gas mixture may be an optical measuring cell based on infrared absorption spectroscopy, wherein is it used both to measure the inspiratory gas mixture in the inspiration line and to measure the expiration gas mixture in the expiration line.

A central measuring and control unit is preferably provided that has final control elements at the evaporator or evaporators to set the perfluorocarbon/oxygen concentration in the inspiratory breathing gas mixture as a function of the perfluorocarbon concentration in the inspiratory and/or expiratory breathing gas mixture. An additional gas-metering unit may be provided for metering one or more additional gases to the inspiratory breathing gas mixture, wherein the metering is set via the measuring and control unit.

An essential advantage of the present invention is that perfluorocarbons with their favorable properties can be used specifically and reproducibly for the treatment of lung diseases.

Completely fluorinated, i.e., hydrogen-free fluorocarbons are also called perfluorinated fluorohydrocarbons or perfluorocarbons (PFC) for short.

These compounds are highly stable and behave almost like noble gases of a similar mass. Advantageous physiological properties were reported in mammals, so that the controlled use is desirable in humans as well.

The breathing gas mixture according to the invention contains an amount of gaseous or vapor-like perfluorocarbon and oxygen with 5 vol. % to 40 vol. % and especially 10 vol. % to 20 vol. % of perfluorocarbon relative to the amount of perfluorocarbon and oxygen in the breathing gas mixture.

The amount corresponding to the sum of perfluorocarbon and oxygen in the breathing gas mixture is about 20 vol. % and, in the extreme case, 100 vol. %, and the rest, amounting to a maximum of about 80 vol. %, contains one or more of the gases nitrogen, nitrogen monoxide and/or one or more anesthesia gases or noble gases, especially xenon.

The preferred perfluorocarbons according to the present invention are perfluoropentane, perfluorohexane, perfluorooctane, alone or as a mixture, and especially perfluorohexane.

It is essential for the present invention that the perfluorocarbons used are used in the form of gases or vapors.

Besides the perfluorocarbons mentioned, it is also possible to use perfluoro-Decalin and perfluorooctyl bromide.

Based on their physicochemical properties (boiling point, vapor pressure), perfluorohexane is best suited for evaporation at usual room temperatures and thus for the use according to the present invention, because the evaporation behavior of perfluorohexane is similar to that of the anesthetics used in clinical practice.

From this arises the great advantage that components that are, in principle, available and may be used in the configurations known from anesthesia may be used for a device for administering a breathing gas mixture according to the present invention.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which preferred embodiments of the invention are illustrated.

BRIEF DESCRIPTION OF THE DRAWINGS

In the drawing:

The only FIGURE is a schematic view of a device according to the invention.

DESCRIPTION OF THE PREFERRED EMBODIMENT

Referring to the drawing in particular, Liquid perfluorohexane 1 is evaporated by means of two series-connected evaporators 2, 3 for volatile anesthetics, which are, however, liquid at room temperature, the evaporators being, in principle, prior-art evaporators.

Evaporators 2, 3 operating according to the bypass principle were used in this case. A carrier gas, specifically oxygen in this case, is introduced into the evaporator or evaporators 2, 3, and the splitting of the carrier gas flow into two partial flows can be set due to the bypass design, so that a partial flow of varying size flows unhindered through the evaporator 2, 3, while the other partial flow is sent into the evaporator chamber filled with the liquid perfluorohexane 1. The vapor pressure and the saturation concentration are constant in this evaporation chamber as long as liquid perfluorohexane 1 is available and the temperature is constant.

Compensation mechanisms of various designs have been known for ensuring the temperature constancy or temperature compensation, so that the metering of the evaporated perfluorohexane ultimately depends only on the ratio of the partial flows, which is set with mechanical regulators or metering valves. The partial flows are again merged behind the evaporator chamber when viewed in the direction of gas flow. Due to the series connection of two or more evaporators 2, 3 and optionally by an additional heating in the evaporator or evaporators 2, 3, it is possible to increase the percentage of evaporated perfluorohexane in the oxygen/perfluorohexane mixture up to about 40 vol. %.

The mixture of evaporated perfluorohexane and oxygen may be mixed with up to 80 vol. % of one or more of the gases nitrogen, nitrogen monoxide and/or one or more anesthesia or noble gases, especially xenon, preferably in a gas-metering unit 4 arranged downstream of the evaporators 2, 3. The breathing gas mixture, which is ultimately fed to the patient P via an inspiration line 5 of a respirator or anesthesia apparatus and is removed via an expiration line 6, consists, in particular, only of the two gas components perfluorohexane and oxygen.

In the exemplary embodiment described, an infrared optical measuring cell 7 is preferably used to determine the concentration of the gaseous perfluorohexane in both the inspiratory breathing gas flow and the expiratory breathing gas flow. The light absorption is measured at one or more infrared wavelengths characteristic of the substance as an indicator of the concentration of the gas in question, here perfluorohexane.

The metering of perfluorohexane/oxygen may be carried out in a controlled manner, e.g., such that, on the one hand, the inspiratory perfluorohexane concentration is compared with the expiratory perfluorohexane concentration based on preset threshold values and the inspiratory concentration is adjusted depending on the difference, especially by means of metering valves at the evaporators 2, 3. As an alternative, the respiration may be carried out with a perfluorohexane concentration set at a fixed value, in which case the concentration measurement of the gaseous perfluorohexane is performed to monitor the treatment. The metering may also be performed by means of a central measuring and control unit 8 at the anesthesia apparatus or respirator. In this case, the measured signals of the measuring cell 7 are converted in the measuring and control unit 8 into control signals for setting the perfluorohexane/oxygen concentration at the evaporators 2, 3 and optionally additionally for setting the gas-metering unit 4 after comparison with preset threshold values and as a function of the breathing pattern for the patient P. Using the breathing gas composition described, a substantially improved, controlled oxygen uptake in the lungs was able to be observed in patients respirated with that breathing gas, and the current drawbacks related to the method of introducing the liquid perfluorohexane directly into the lungs were avoided at the same time.

The absolute metering per treatment is set and determined based on the parameters body weight, duration and type of respiration as well as the perfluorohexane concentration in the inspiratory and expiratory gas volume flows.

While specific embodiments of the invention have been shown and described in detail to illustrate the application of the principles of the invention, it will be understood that the invention may be embodied otherwise without departing from such principles.

What is claimed is:

1. A breathing gas mixture, comprising an amount of perfluorocarbon and oxygen with 5 vol. % to 40 vol. % perfluorocarbon relative to the amount of perfluorocarbon and oxygen.

2. The breathing gas mixture in accordance with claim 1, wherein the percentage of perfluorocarbon and oxygen in the breathing gas mixture is about 20 vol. % to 100 vol. % of the breathing gas mixture and the remaining part of up to about 80 vol. % contains one or more of the gases nitrogen, nitrogen monoxide and/or one or more anesthesia gases or noble gases, especially xenon.

3. The breathing gas mixture in accordance with claim 1, wherein the perfluorocarbon comprises one or more of the compounds perfluoropentane, perfluorohexane, and perfluorooctane.

4. The breathing gas mixture in accordance with claim 3, wherein the perfluorocarbon is perfluorohexane.

5. A breathing gas mixture comprising:
   oxygen gas;
   a perfluorocarbon gas mixed with said oxygen to form an oxygen/perfluorocarbon blend with 5 vol. % to 40 vol. % perfluorocarbon gas.

6. A breathing gas mixture in accordance with claim 5, further comprising:
   additional breathing gas mixed with said oxygen/perfluorocarbon blend, said oxygen/perfluorocarbon blend forming approximately 20 vol. % to 100 vol. % of the breathing gas mixture.

7. A breathing gas mixture in accordance with claim 6, wherein:
   said additional breathing gas includes one or more of nitrogen gas, nitrogen monoxide gas, anesthesia gas and noble gas.

8. A breathing gas mixture in accordance with claim 7, wherein:
   said noble gas includes xenon.

9. A breathing gas mixture in accordance with claim 6, wherein:
   said additional breathing gas includes a plurality of anesthesia gases.

10. A breathing gas mixture in accordance with claim 6, wherein:
    said additional breathing gas includes a plurality of noble gases.

11. A breathing gas mixture in accordance with claim 5, wherein:
    said perfluorocarbon gas comprises one or more of perfluoropentane, perfluorohexane, perfluorooctane, perfluoro-Decalin and perfluorooctyl bromide.

12. A breathing gas mixture in accordance with claim 5, wherein:

said perfluorocarbon comprises one or more of perfluoropentane, perfluorooctane, perfluoro-Decalin and perfluorooctyl bromide.

13. A breathing gas mixture in accordance with claim 8, wherein:

said perfluorocarbon comprises one or more of perfluoropentane, perfluorohexane, perfluorooctane, perfluoro-Decalin and perfluorooctyl bromide;

said additional breathing gas includes a plurality of anesthesia gases and a plurality of noble gases.

* * * * *